US011717361B2

(12) United States Patent
Rockrohr (10) Patent No.: US 11,717,361 B2
(45) Date of Patent: Aug. 8, 2023

(54) ELECTROSURGICAL ROBOTIC SYSTEM HAVING TOOL PRESENCE DETECTION

(71) Applicant: Covidien LP, Mansfield, MA (US)

(72) Inventor: Brian Rockrohr, Guilford, CT (US)

(73) Assignee: Covidien LP, Mansfield, MA (US)

( * ) Notice: Subject to any disclaimer, the term of this patent is extended or adjusted under 35 U.S.C. 154(b) by 814 days.

(21) Appl. No.: 16/611,247

(22) PCT Filed: May 7, 2018

(86) PCT No.: PCT/US2018/031292
§ 371 (c)(1),
(2) Date: Nov. 6, 2019

(87) PCT Pub. No.: WO2018/217429
PCT Pub. Date: Nov. 29, 2018

(65) Prior Publication Data
US 2020/0155251 A1 May 21, 2020

Related U.S. Application Data

(60) Provisional application No. 62/510,567, filed on May 24, 2017.

(51) Int. Cl.
*A61B 34/35* (2016.01)
*A61B 18/14* (2006.01)
*A61B 18/00* (2006.01)
(52) U.S. Cl.
CPC .......... *A61B 34/35* (2016.02); *A61B 18/1445* (2013.01); *A61B 2018/00178* (2013.01);
(Continued)

(58) Field of Classification Search
CPC ............... A61B 34/35; A61B 18/1445; A61B 2018/00178; A61B 2018/00577; A61B 2018/00589; A61B 2018/00601
See application file for complete search history.

(56) References Cited

U.S. PATENT DOCUMENTS

| 6,132,368 A | 10/2000 | Cooper |
| 6,206,903 B1 | 3/2001 | Ramans |

(Continued)

FOREIGN PATENT DOCUMENTS

| CN | 101443162 A | * 5/2009 | ............. A61B 34/30 |
| CN | 111989053 A | * 11/2020 | ....... A61B 17/00234 |

(Continued)

OTHER PUBLICATIONS

Chinese First Office Action dated May 18, 2022 issued in counterpart Patent Application CN 2018800327700.

(Continued)

*Primary Examiner* — Jeffrey T Carley
(74) *Attorney, Agent, or Firm* — Carter, DeLuca & Farrell LLP (57) ABSTRACT

A robotic system includes an electrosurgical generator; an electrosurgical instrument including an electrosurgical connector; and a robotic arm having an instrument drive unit coupled to the electrosurgical instrument. The instrument drive unit includes a drive unit housing having: an electrosurgical receptacle coupled to the electrosurgical generator and configured to engage the electrosurgical connector; an activation link configured to engage the electrosurgical connector; and a detection switch actuatable by the actuation link upon being engaged by the electrosurgical connector.

7 Claims, 5 Drawing Sheets

(52) U.S. Cl.
CPC .............. *A61B 2018/00577* (2013.01); *A61B 2018/00589* (2013.01); *A61B 2018/00601* (2013.01)

(56) References Cited

U.S. PATENT DOCUMENTS

| | | | |
|---|---|---|---|
| 6,246,200 B1 | 6/2001 | Blumenkranz et al. | |
| 6,312,435 B1 | 11/2001 | Wallace et al. | |
| 6,331,181 B1 | 12/2001 | Tierney et al. | |
| 6,394,998 B1 | 5/2002 | Wallace et al. | |
| 6,424,885 B1 | 7/2002 | Niemeyer et al. | |
| 6,434,507 B1 * | 8/2002 | Clayton | A61B 17/32002 600/117 |
| 6,441,577 B2 | 8/2002 | Blumenkranz et al. | |
| 6,459,926 B1 | 10/2002 | Nowlin et al. | |
| 6,491,691 B1 | 12/2002 | Morley et al. | |
| 6,491,701 B2 | 12/2002 | Tierney et al. | |
| 6,493,608 B1 | 12/2002 | Niemeyer | |
| 6,565,554 B1 | 5/2003 | Niemeyer | |
| 6,645,196 B1 | 11/2003 | Nixon et al. | |
| 6,659,939 B2 | 12/2003 | Moll | |
| 6,671,581 B2 | 12/2003 | Niemeyer et al. | |
| 6,676,684 B1 | 1/2004 | Morley et al. | |
| 6,685,698 B2 | 2/2004 | Morley et al. | |
| 6,699,235 B2 | 3/2004 | Wallace et al. | |
| 6,714,839 B2 | 3/2004 | Salisbury, Jr. et al. | |
| 6,716,233 B1 | 4/2004 | Whitman | |
| 6,728,599 B2 | 4/2004 | Wang et al. | |
| 6,746,443 B1 | 6/2004 | Morley et al. | |
| 6,766,204 B2 | 7/2004 | Niemeyer et al. | |
| 6,770,081 B1 | 8/2004 | Cooper et al. | |
| 6,772,053 B2 | 8/2004 | Niemeyer | |
| 6,783,524 B2 | 8/2004 | Anderson et al. | |
| 6,793,652 B1 | 9/2004 | Whitman et al. | |
| 6,793,653 B2 | 9/2004 | Sanchez et al. | |
| 6,799,065 B1 | 9/2004 | Niemeyer | |
| 6,837,883 B2 | 1/2005 | Moll et al. | |
| 6,839,612 B2 | 1/2005 | Sanchez et al. | |
| 6,840,938 B1 | 1/2005 | Morley et al. | |
| 6,843,403 B2 | 1/2005 | Whitman | |
| 6,846,309 B2 | 1/2005 | Whitman et al. | |
| 6,866,671 B2 | 3/2005 | Tierney et al. | |
| 6,871,117 B2 | 3/2005 | Wang et al. | |
| 6,879,880 B2 | 4/2005 | Nowlin et al. | |
| 6,899,705 B2 | 5/2005 | Niemeyer | |
| 6,902,560 B1 | 6/2005 | Morley et al. | |
| 6,936,042 B2 | 8/2005 | Wallace et al. | |
| 6,951,535 B2 | 10/2005 | Ghodoussi et al. | |
| 6,974,449 B2 | 12/2005 | Niemeyer | |
| 6,991,627 B2 | 1/2006 | Madhani et al. | |
| 6,994,708 B2 | 2/2006 | Manzo | |
| 7,048,745 B2 | 5/2006 | Tierney et al. | |
| 7,066,926 B2 | 6/2006 | Wallace et al. | |
| 7,118,582 B1 | 10/2006 | Wang et al. | |
| 7,125,403 B2 | 10/2006 | Julian et al. | |
| 7,155,315 B2 | 12/2006 | Niemeyer et al. | |
| 7,239,940 B2 | 7/2007 | Wang et al. | |
| 7,306,597 B2 | 12/2007 | Manzo | |
| 7,357,774 B2 | 4/2008 | Cooper | |
| 7,373,219 B2 | 5/2008 | Nowlin et al. | |
| 7,379,790 B2 | 5/2008 | Toth et al. | |
| 7,386,365 B2 | 6/2008 | Nixon | |
| 7,391,173 B2 | 6/2008 | Schena | |
| 7,398,707 B2 | 7/2008 | Morley et al. | |
| 7,413,565 B2 | 8/2008 | Wang et al. | |
| 7,453,227 B2 | 11/2008 | Prisco et al. | |
| 7,524,320 B2 | 4/2009 | Tierney et al. | |
| 7,574,250 B2 | 8/2009 | Niemeyer | |
| 7,594,912 B2 | 9/2009 | Cooper et al. | |
| 7,607,440 B2 | 10/2009 | Coste-Maniere et al. | |
| 7,666,191 B2 | 2/2010 | Orban, III et al. | |
| 7,682,357 B2 | 3/2010 | Ghodoussi et al. | |
| 7,689,320 B2 | 3/2010 | Prisco et al. | |
| 7,695,481 B2 | 4/2010 | Wang et al. | |
| 7,695,485 B2 | 4/2010 | Whitman et al. | |
| 7,699,855 B2 | 4/2010 | Anderson et al. | |
| 7,713,263 B2 | 5/2010 | Niemeyer | |
| 7,725,214 B2 | 5/2010 | Diolaiti | |
| 7,727,244 B2 | 6/2010 | Orban, III et al. | |
| 7,741,802 B2 | 6/2010 | Prisco | |
| 7,756,036 B2 | 7/2010 | Druke et al. | |
| 7,757,028 B2 | 7/2010 | Druke et al. | |
| 7,762,825 B2 | 7/2010 | Burbank et al. | |
| 7,778,733 B2 | 8/2010 | Nowlin et al. | |
| 7,803,151 B2 | 9/2010 | Whitman | |
| 7,806,891 B2 | 10/2010 | Nowlin et al. | |
| 7,819,859 B2 | 10/2010 | Prisco et al. | |
| 7,819,885 B2 | 10/2010 | Cooper | |
| 7,824,401 B2 | 11/2010 | Manzo et al. | |
| 7,835,823 B2 | 11/2010 | Sillman et al. | |
| 7,843,158 B2 | 11/2010 | Prisco | |
| 7,865,266 B2 | 1/2011 | Moll et al. | |
| 7,865,269 B2 | 1/2011 | Prisco et al. | |
| 7,886,743 B2 | 2/2011 | Cooper et al. | |
| 7,899,578 B2 | 3/2011 | Prisco et al. | |
| 7,907,166 B2 | 3/2011 | Lamprecht et al. | |
| 7,935,130 B2 | 5/2011 | Williams | |
| 7,963,913 B2 | 6/2011 | Devengenzo et al. | |
| 7,983,793 B2 | 7/2011 | Toth et al. | |
| 8,002,767 B2 | 8/2011 | Sanchez | |
| 8,004,229 B2 | 8/2011 | Nowlin et al. | |
| 8,012,170 B2 | 9/2011 | Whitman et al. | |
| 8,054,752 B2 | 11/2011 | Druke et al. | |
| 8,062,288 B2 | 11/2011 | Cooper et al. | |
| 8,079,950 B2 | 12/2011 | Stern et al. | |
| 8,100,133 B2 | 1/2012 | Mintz et al. | |
| 8,108,072 B2 | 1/2012 | Zhao et al. | |
| 8,120,301 B2 | 2/2012 | Goldberg et al. | |
| 8,142,447 B2 | 3/2012 | Cooper et al. | |
| 8,147,503 B2 | 4/2012 | Zhao et al. | |
| 8,151,661 B2 | 4/2012 | Schena et al. | |
| 8,155,479 B2 | 4/2012 | Hoffman et al. | |
| 8,182,469 B2 | 5/2012 | Anderson et al. | |
| 8,202,278 B2 | 6/2012 | Orban, III et al. | |
| 8,206,406 B2 | 6/2012 | Orban, III | |
| 8,210,413 B2 | 7/2012 | Whitman et al. | |
| 8,216,250 B2 | 7/2012 | Orban, III et al. | |
| 8,220,468 B2 | 7/2012 | Cooper et al. | |
| 8,256,319 B2 | 9/2012 | Cooper et al. | |
| 8,285,517 B2 | 10/2012 | Sillman et al. | |
| 8,315,720 B2 | 11/2012 | Mohr et al. | |
| 8,335,590 B2 | 12/2012 | Costa et al. | |
| 8,347,757 B2 | 1/2013 | Duval | |
| 8,374,723 B2 | 2/2013 | Zhao et al. | |
| 8,418,073 B2 | 4/2013 | Mohr et al. | |
| 8,419,717 B2 | 4/2013 | Diolaiti et al. | |
| 8,423,182 B2 | 4/2013 | Robinson et al. | |
| 8,452,447 B2 | 5/2013 | Nixon | |
| 8,454,585 B2 | 6/2013 | Whitman | |
| 8,499,992 B2 | 8/2013 | Whitman et al. | |
| 8,508,173 B2 | 8/2013 | Goldberg et al. | |
| 8,528,440 B2 | 9/2013 | Morley et al. | |
| 8,529,582 B2 | 9/2013 | Devengenzo et al. | |
| 8,540,748 B2 | 9/2013 | Murphy et al. | |
| 8,551,116 B2 | 10/2013 | Julian et al. | |
| 8,562,594 B2 | 10/2013 | Cooper et al. | |
| 8,594,841 B2 | 11/2013 | Zhao et al. | |
| 8,597,182 B2 | 12/2013 | Stein et al. | |
| 8,597,280 B2 | 12/2013 | Cooper et al. | |
| 8,600,551 B2 | 12/2013 | Itkowitz et al. | |
| 8,608,773 B2 | 12/2013 | Tierney et al. | |
| 8,620,473 B2 | 12/2013 | Diolaiti et al. | |
| 8,624,537 B2 | 1/2014 | Nowlin et al. | |
| 8,634,957 B2 | 1/2014 | Toth et al. | |
| 8,638,056 B2 | 1/2014 | Goldberg et al. | |
| 8,638,057 B2 | 1/2014 | Goldberg et al. | |
| 8,644,988 B2 | 2/2014 | Prisco et al. | |
| 8,666,544 B2 | 3/2014 | Moll et al. | |
| 8,668,638 B2 | 3/2014 | Donhowe et al. | |
| 8,746,252 B2 | 6/2014 | McGrogan et al. | |
| 8,749,189 B2 | 6/2014 | Nowlin et al. | |
| 8,749,190 B2 | 6/2014 | Nowlin et al. | |
| 8,758,352 B2 | 6/2014 | Cooper et al. | |
| 8,761,930 B2 | 6/2014 | Nixon | |

(56) References Cited

U.S. PATENT DOCUMENTS

| | | |
|---|---|---|
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,828,023 B2 | 9/2014 | Neff et al. |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart |
| 8,989,903 B2 | 3/2015 | Weir et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,028 B2 | 3/2016 | Johnson |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |

(56) References Cited

U.S. PATENT DOCUMENTS

| | | |
|---|---|---|
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Diolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,274 B2 | 6/2021 | Dachs, II et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 2009/0163929 A1* | 6/2009 | Yeung ............... B25J 9/047 606/130 |
| 2010/0225209 A1* | 9/2010 | Goldberg ............ G16H 20/40 312/209 |
| 2013/0267950 A1* | 10/2013 | Rosa ............... A61B 18/1233 606/45 |
| 2013/0324979 A1* | 12/2013 | Nicholas ............ A61B 17/068 606/1 |
| 2014/0128886 A1* | 5/2014 | Holop ................ A61B 18/14 901/41 |
| 2015/0105800 A1* | 4/2015 | Lohmeier ............ A61B 46/10 606/130 |
| 2016/0270839 A1* | 9/2016 | Stewart ............ A61B 18/1445 |
| 2016/0346513 A1* | 12/2016 | Swaney ............ A61B 17/3417 |
| 2018/0079090 A1* | 3/2018 | Koenig ............... G16H 40/63 |
| 2018/0256235 A1* | 9/2018 | Cohen ................ A61B 90/98 |
| 2018/0325582 A1* | 11/2018 | Goodman .......... A61B 18/1442 |

FOREIGN PATENT DOCUMENTS

| | | | |
|---|---|---|---|
| EP | 1647234 A1 | 4/2006 | |
| EP | 1897511 A2 * | 3/2008 | ............ A61B 34/30 |
| EP | 2082694 A1 * | 7/2009 | ............ A61B 18/18 |
| WO | 2014071184 A1 | 5/2014 | |

OTHER PUBLICATIONS

Extended European Search Report dated Jan. 19, 2021 issued in corresponding EP Appln. No 18806238.4.

\* cited by examiner

ELECTROSURGICAL ROBOTIC SYSTEM HAVING TOOL PRESENCE DETECTION

CROSS-REFERENCE TO RELATED APPLICATIONS

This application is a National Stage Application of PCT/US2018/031292 under 35 USC § 371 (a), filed May 7, 2018, which claims benefit of and priority to U.S. Provisional Patent Application Ser. No. 62/510,567, filed May 24, 2017, the disclosures of each of the above-identified applications are hereby incorporated by reference in their entirety.

BACKGROUND

Robotic surgical systems are currently being used in minimally invasive medical procedures. Some robotic surgical systems may include a console supporting a surgical robotic arm and a surgical instrument having an end effector (e.g., forceps or grasping tool) mounted to the robotic arm. The robotic arm provides mechanical power to the surgical instrument for its operation and movement.

Robotic surgical systems also operate with electrosurgical devices. Electrosurgery involves application of high radio frequency electrical current to a surgical site to cut, ablate, desiccate, or coagulate tissue. In monopolar electrosurgery, a source or active electrode delivers radio frequency alternating current from an electrosurgical generator to the targeted tissue. A patient return electrode is placed remotely from the active electrode to conduct the current back to the generator.

In bipolar electrosurgery, return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes.

When using electrosurgical devices with robotic systems, wires connecting these devices to the electrosurgical generator may wrap around the robotic arm. Thus, there is a need for an improved system of coupling electrosurgical devices to the robotic surgical systems.

SUMMARY

According to one embodiment of the present disclosure, an apparatus for electrically connecting a robotically controlled electrosurgical instrument to an electrosurgical generator is disclosed. The apparatus includes an electrosurgical connector and a robotic drive unit housing, which includes: an electrosurgical receptacle configured to engage the electrosurgical connector; an activation link having a first segment configured to engage the electrosurgical connector and a second segment; and a detection switch actuatable by the second segment upon the first segment being engaged by the electrosurgical connector.

According to one aspect of the above embodiment, the electrosurgical receptacle is a monopolar receptacle having a contact configured to electrically couple to the electrosurgical connector.

According to another aspect of the above embodiment, the activation link may include a bent portion interconnecting the first segment and the second segment and the first and second segments are configured to flex about the bent portion. One of the first segment or the second segment may include a deformable portion that is configured to flex in response to the first segment being engaged by the electrosurgical connector being fully engaged with the electrosurgical receptacle. The first segment may include a protrusion disposed in a path of engagement by the electrosurgical connector and configured to contact the electrosurgical connector.

According to another embodiment of the present disclosure, an apparatus for electrically connecting a robotically controlled electrosurgical instrument to an electrosurgical generator is disclosed. The apparatus includes an electrosurgical connector and a robotic drive unit housing having: an electrosurgical receptacle configured to engage the electrosurgical connector; a connector link configured to engage the electrosurgical connector; an activation link having a first segment configured to engage the connector link and a second segment; and a detection switch actuatable by the second segment upon the first segment being engaged by the connector link.

According to one aspect of the above embodiment, the electrosurgical receptacle is a bipolar receptacle having an active contact and a return contact that are configured to electrically couple to the electrosurgical connector.

According to another aspect of the above embodiment, the activation link includes a middle segment interconnecting the first segment and the second segment. The activation link may also include a first curved portion interconnecting the first segment and the middle segment and a second curved portion interconnecting the second segment and the middle segment.

According to a further embodiment of the present disclosure, a robotic surgical system is disclosed. The robotic system includes an electrosurgical generator; an electrosurgical instrument including an electrosurgical connector; and a robotic arm having an instrument drive unit coupled to the electrosurgical instrument. The instrument drive unit includes a drive unit housing having: an electrosurgical receptacle coupled to the electrosurgical generator and configured to engage the electrosurgical connector; an activation link configured to engage the electrosurgical connector; and a detection switch actuatable by the actuation link upon being engaged by the electrosurgical connector.

According to one aspect of the above embodiment, the electrosurgical instrument is a monopolar electrosurgical instrument and the electrosurgical receptacle includes an electrical contact configured to couple to the electrosurgical connector.

According to another aspect of the above embodiment, the electrosurgical instrument is a bipolar electrosurgical instrument and the electrosurgical receptacle includes an active contact and a return contact that are configured to electrically couple to the electrosurgical connector.

According to a further aspect of the above embodiment, the activation link includes a first segment configured to engage the electrosurgical connector and a second segment configured to actuate the detection switch. The activation link may include a bent portion interconnecting the first segment and the second segment, the first and second segments configured to flex about the bent portion. One of the first segment or the second segment may include a deformable portion that is configured to flex in response to the first segment being engaged by the electrosurgical connector being fully engaged with the electrosurgical receptacle. The first segment may include a protrusion disposed in a path of engagement by the electrosurgical connector and configured to contact the electrosurgical connector.

According to one aspect of the above embodiment, the robotic drive unit housing may further include a connector link configured to engage the electrosurgical connector. The second segment of the activation link may be configured to actuate the connector link. The activation link may also include a middle segment interconnecting the first segment and the second segment. The activation link may further include a first curved portion interconnecting the first segment and the middle segment and a second curved portion interconnecting the second segment and the middle segment.

BRIEF DESCRIPTION OF THE DRAWINGS

Embodiments of the present disclosure are described herein with reference to the accompanying drawings, wherein.

DETAILED DESCRIPTION

Embodiments of the presently disclosed robotic surgical assembly are described in detail with reference to the drawings, in which like reference numerals designate identical or corresponding elements in each of the several views. As used herein the term "distal" refers to the portion of the robotic surgical assembly and/or the surgical instrument coupled thereto that is closer to the patient, while the term "proximal" refers to the portion that is farther from the patient.

As will be described in detail below, the present disclosure is directed to a robotic surgical system for use with an electrosurgical generator. The robotic surgical system includes a surgical robotic arm having an electrosurgical instrument, which is coupled to and powered by the electrosurgical generator. The electrosurgical instrument includes an electrosurgical connector configured to couple to an electrosurgical receptacle receiving power from the electrosurgical generator. The electrosurgical receptacle includes an activation link configured to engage the electrosurgical connector and a detection switch actuatable by the actuation link upon being engaged by the electrosurgical connector. Actuation of the detection switch signals the electrosurgical generator that the electrosurgical connector of the electrosurgical instrument is properly connected to the electrosurgical receptacle.

Figure 1:
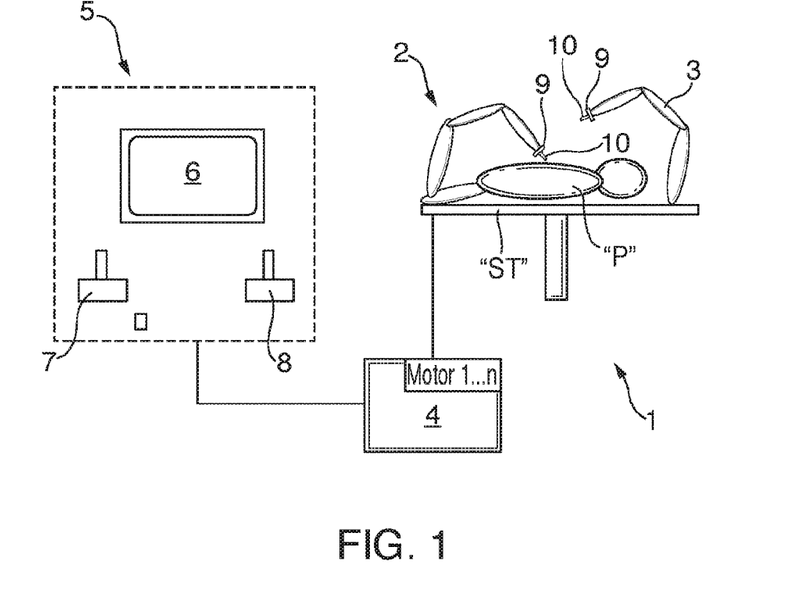
FIG. 1 is a schematic illustration of a robotic surgical system including a robotic surgical assembly according to the present disclosure.

Referring initially to FIG. 1, a robotic surgical system 1 includes a plurality of surgical robotic arms 2, 3 having an electrosurgical instrument 10 removably attached thereto; a control device 4; and an operating console 5 coupled to control device 4. Robotic surgical system 1 is configured for use on a patient "P" lying on a surgical table "ST" to be treated in a minimally invasive manner using a surgical instrument, e.g., electrosurgical instrument 10.

Operating console 5 includes a display device 6, which displays the surgical site and manual input devices 7, 8, by which a clinician is able to telemanipulate robotic arms 2, 3. Each of the robotic arms 2, 3 may be composed of a plurality of members, which are connected through joints. Robotic arms 2, 3 may be driven by electric drives (not shown) that are connected to control device 4. Control device 4 (e.g., a computer) is set up to activate the drives, based on a set of programmable instructions stored in memory, in such a way that robotic arms 2, 3 and electrosurgical instruments 10 execute a desired movement according to a movement in response to input from manual input devices 7, 8.

Control device 4 may control a plurality of motors (e.g., motor 1 . . . n), each of which is configured to actuate an electrosurgical instrument 10 to effect operation and/or movement of electrosurgical instrument 10. It is contemplated that control device 4 coordinates the activation of the various motors (motor 1 . . . n) to coordinate a clockwise or counter-clockwise rotation of drive members (not shown) to coordinate an operation and/or movement of the electrosurgical instrument 10. In embodiments, each motor of the plurality of motors (motor 1 . . . n) can be configured to actuate a drive rod or a lever arm (not shown) to effect operation and/or movement of each electrosurgical instrument 10.

For a detailed discussion of the construction and operation of a robotic surgical system, reference may be made to U.S. Pat. No. 8,828,023, filed on Nov. 3, 2011, entitled "Medical Workstation," the entire contents of which are incorporated herein by reference.

Figure 2:
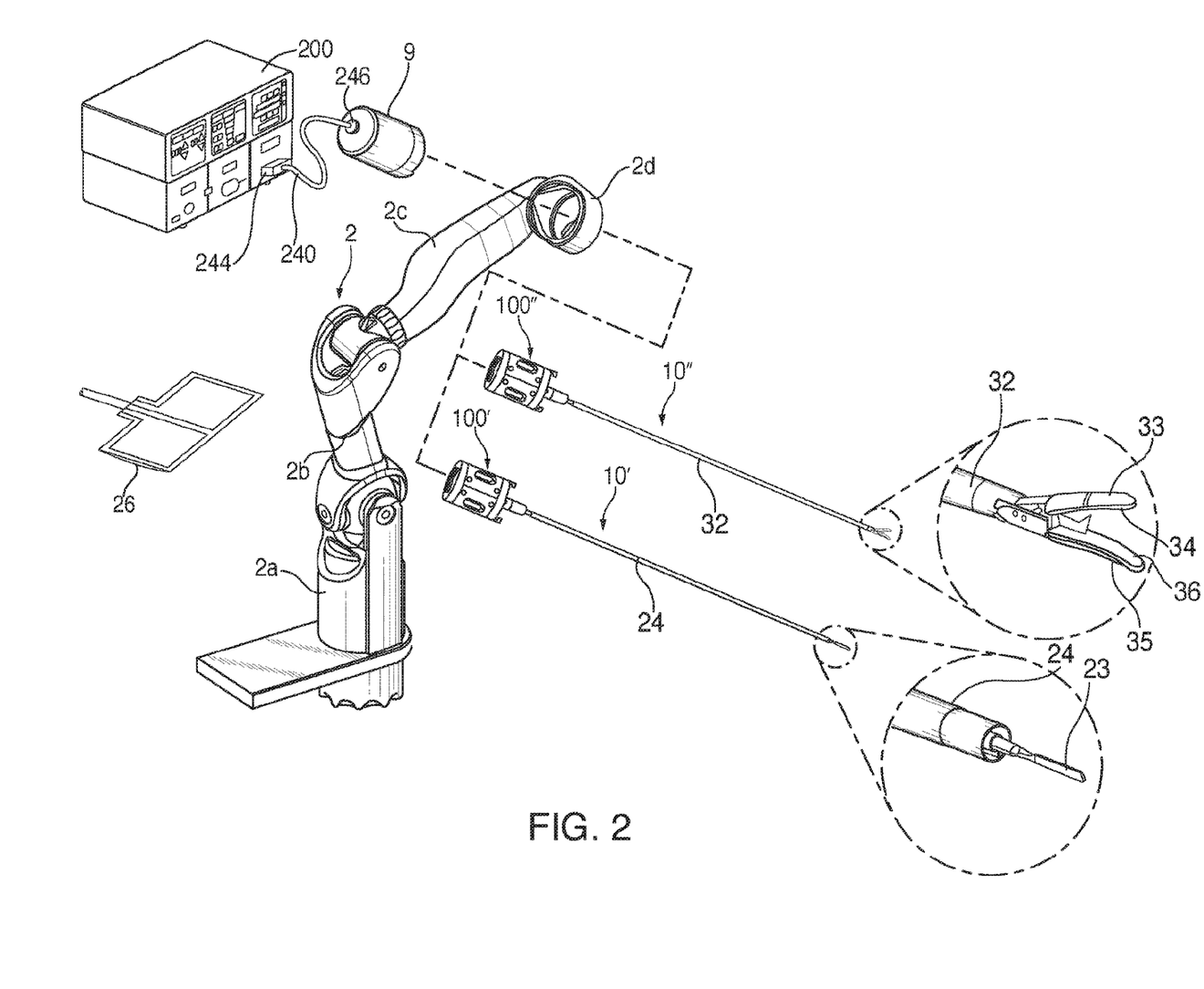
FIG. 2 is a perspective view of the robotic surgical assembly of FIG. 1 and an electrosurgical generator.

With reference to FIG. 2, the robotic arm 2 includes a base 2a, a plurality of segments 2b and 2c, and a holder 2d, which are coupled to each other by actuators (not shown) allowing for movement of the robotic arm 2 into various configurations. The holder 2d is configured to receive an instrument drive unit 9 which is configured to couple to an actuation mechanism 100' or 100" that is coupled to a monopolar electrosurgical instrument 10' or a bipolar electrosurgical instrument 10", respectively. Instrument drive unit 9 transfers actuation forces from its motors (not shown) to actuation mechanism 100'/100" of electrosurgical instruments 10'/10" to drive movement of components of electrosurgical end effectors, e.g., active electrode 23 of monopolar electrosurgical instrument 10' or opposing jaw members 33 and 35 of bipolar electrosurgical instrument 10". Instrument drive unit 9 includes a plurality of driving members (not shown) attached to a respective motor (not shown) such that the drive members are independently rotatable with respect to one another.

The monopolar electrosurgical instrument 10' includes one or more active electrodes 23, e.g., electrosurgical cutting probe, ablation electrode(s), etc., for treating tissue of a patient. The electrode 23 is disposed at a distal end of a shaft 24. Electrosurgical alternating RF current is supplied to the monopolar electrosurgical instrument 10' by a generator 200 through an active terminal 230 (FIG. 3) of the generator 200, allowing the instrument 10' to cut, coagulate, thermally or non-thermally ablate and/or otherwise treat tissue. The alternating current is returned to the generator 200 through a return electrode pad 26 through a return terminal 232 (FIG. 3) of the generator 200. For monopolar operation, the system 1 may include a plurality of return electrode pads 26 that, in use, are disposed on a patient to minimize the chances of tissue damage by maximizing the overall contact area with the patient. In addition, the generator 200 and the return electrode pads 26 may be configured for monitoring tissue-to-patient contact.

Figure 3:
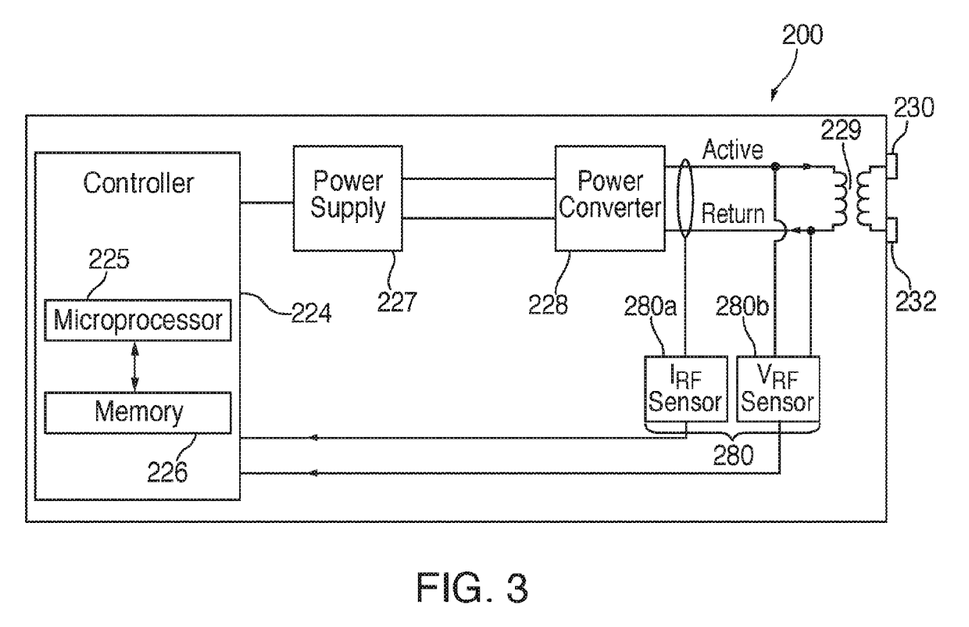
FIG. 3 is a schematic diagram of the electrosurgical generator of FIG. 2.

The bipolar electrosurgical instrument 10″ may be a bipolar electrosurgical forceps having one or more electrodes for treating tissue of a patient. The bipolar electrosurgical instrument 10″ includes opposing jaw members 33 and 35 disposed at a distal portion of a shaft 32. The jaw members 33 and 35 have one or more active electrodes 34 and a return electrode 36 disposed therein, respectively. The active electrode 34 and the return electrode 36 are connected to the generator 200 through the active and return terminals 230, 232, respectively (FIG. 3).

The generator 200 may be coupled to the control device 4 (FIG. 1) such that the control device 4 may monitor and/or operate the generator 200. With reference to FIG. 3, the generator 200 may be any suitable electrosurgical generator which includes a controller 224, a power supply 227, and a power converter 228. The power supply 227 may be a high voltage, DC power supply connected to an AC source (e.g., line voltage) and provides high voltage, DC power to the power converter 228, which then converts high voltage, DC power into RF energy and delivers the energy to the active terminal 230. The energy is returned thereto via the return terminal 232. In particular, electrosurgical energy for energizing the electrosurgical instrument 10′/10″ is delivered through the active and return terminals 230 and 232. The active and return terminals 230 and 232 may be coupled to the power converter 228 through an isolation transformer 229. It is contemplated that the isolation transformer 229 may be optional and alternatively, the active and return terminals 230 and 232 may be coupled directly to converter 228.

The controller 224 includes a processor 225 operably connected to a memory 226, which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor 225 may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor 225 may be any logic processor (e.g., control circuit) adapted to perform the calculations and/or set of instructions described herein.

The controller 224 includes an output port (not shown) that is operably connected to the power supply 227 and/or power converter 228 allowing the processor 225 to control the output of the generator 200 according to either open and/or closed control loop schemes. A closed loop control scheme is a feedback control loop, in which a plurality of sensors measure a variety of tissue and energy properties (e.g., tissue impedance, tissue temperature, output power, current and/or voltage, etc.), and provide feedback to the controller 224. The controller 224 then controls the power supply 227 and/or power converter 228, which adjusts the DC and/or power supply, respectively.

The generator 200 according to the present disclosure may also include a plurality of sensors 280, such a current sensor 280a and a voltage sensor 280b. The sensors 280a and 280b may be coupled to the power supply 227, and/or power converter 228 and may be configured to sense properties of DC current supplied to the power converter 228 and/or RF energy outputted by the power converter 228. Various components of the generator 200, namely, the power converter 228, the current and voltage sensors 280a, 280b, may be disposed on a printed circuit board (PCB). The controller 224 also receives input signals from the input controls of the generator 200 and/or the electrosurgical instrument 10′/10″. The controller 224 utilizes the input signals to adjust power outputted by the generator 200 and/or performs other control functions thereon. U.S. Pat. No. 9,283,028, describes an electrosurgical generator in more detail, the entire contents of which is incorporated by reference herein.

With reference to FIG. 2, the electrosurgical generator 200 provides power to the electrosurgical instrument 10′/10″ via a cable 240. The cable 240 includes a generator connector 244 and a drive unit connector 246. The generator connector 244 is coupled to one or more ports (not shown) of the electrosurgical generator 200. The drive unit connector 246 is coupled to the instrument drive unit 9 such that the electrosurgical instrument 10′/10″ coupled to the instrument drive unit 9 receives electrosurgical power from the generator 200.

Figure 4:
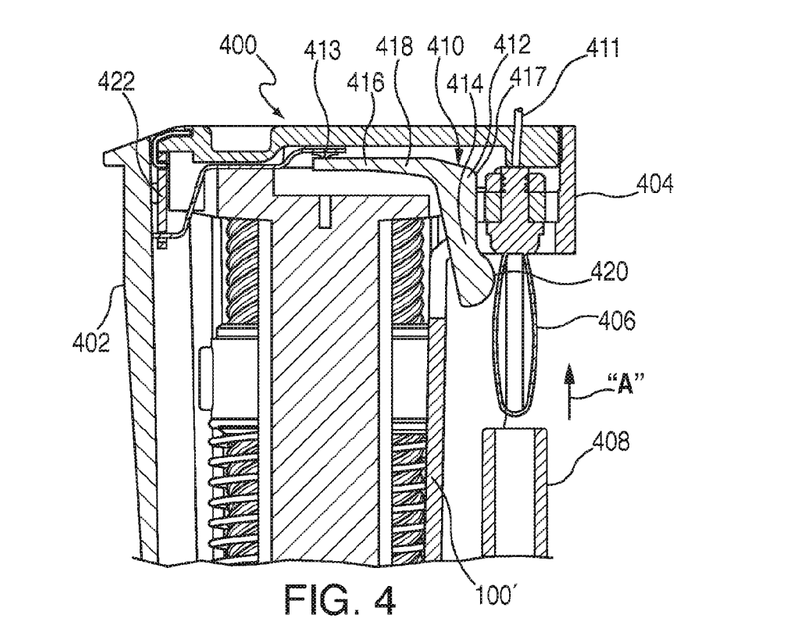
FIG. 4 is a side, cross-sectional view of a monopolar connector shown in a disconnected configuration.
Figure 5:
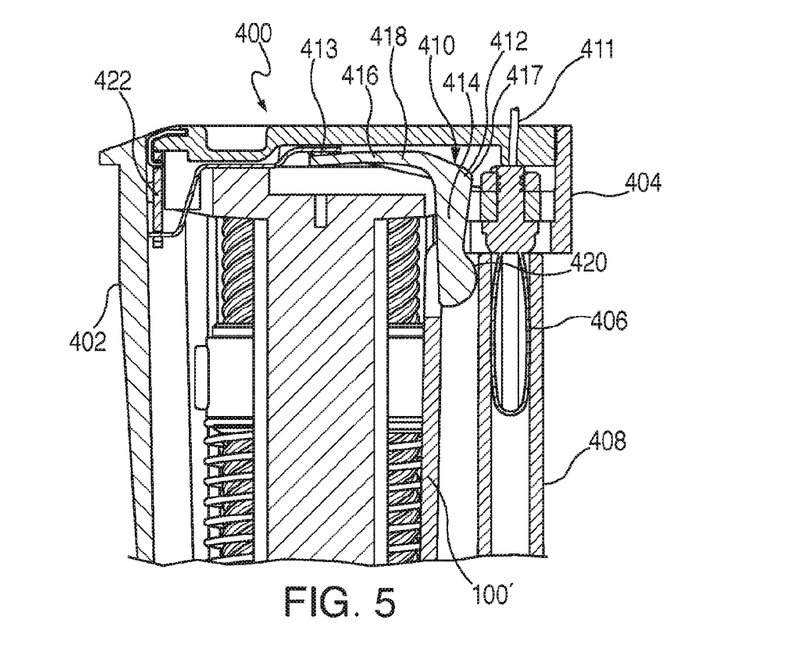
FIG. 5 is a side, cross-sectional view of the monopolar connector of FIG. 4 shown in a connected configuration.

With reference to FIGS. 4 and 5, a monopolar drive unit 400 is shown. The monopolar drive unit 400, which is similar to the instrument drive unit 9 and is also configured to couple to the holder 2d (FIG. 1), includes a drive unit housing 402, which receives the actuation mechanism 100′ therein. The monopolar drive unit 400 also includes a monopolar receptacle 404 electrically coupled to the generator 200 through the cable 240. The monopolar receptacle 404 includes a contact 406, which is configured to couple to a monopolar connector 408. The contact 406 is coupled to one or more leads 411 electrically connecting the active electrode 23 of the monopolar electrosurgical instrument 10′ to the contact 406.

The monopolar drive unit 400 also includes a detection assembly 410 having an activation link 412 configured to engage a detection switch 413 disposed on an inner wall of the drive unit housing 402. In embodiments, the detection switch 413 may be disposed on any surface within the drive unit housing 402 where it may be actuated by the activation link 412. The detection switch 413 may be any suitable electrical switch that may be actuated by physical contact, namely, from the activation link 412, such as a limit switch, a push button switch, and the like. The activation link 412 includes a first segment 414 configured to engage the monopolar connector 408 and a second segment 416 configured to engage the detection switch 413. The activation link 412 may be formed from any suitable flexible or resilient non-conductive material such as polymers. The first segment 414 and the second segment 416 are disposed at any suitable angle relative to each other, which in embodiments, may be larger than 90 degrees. The first segment 414 is interconnected to the second segment 416 via a bent portion 417. In addition, one of the first segment 414 or the second segment 416 also includes a deformable portion 418, which is shown as part of the second segment 416, allowing for flexing or deformation of the second segment 416 relative to the first segment 414. The first segment 414 also includes a protrusion 420 configured to engage the monopolar connector 408.

During use, the monopolar connector 408 is inserted in a direction "A," as shown in FIG. 4, into the monopolar receptacle 404, thereby electrically coupling with the contact 406 of the monopolar receptacle 404. The monopolar connector 408 also engages the activation link 412, in particular, the protrusion 420 of the first segment 414. This engagement pushes the first segment 414 laterally, in a direction perpendicular to the direction "A." This in turn, bends activation link 412 at the bent portion 417 disposed between the first segment 414 and the second segment 416. Since the first segment 414 is fully compressed, the mechanical strain is transferred to the second segment 416, and in particular, the deformable portion 418. The deformable portion 418 of the second segment 416 has a predetermined stiffness, k, defined by a formula (I):

$$k=F/\delta \quad \quad (I)$$

In formula (I), F is the force applied to the deformable portion 418 by the insertion of the monopolar connector 408 and δ is a displacement (e.g., distance) in a direction perpendicular to a longitudinal axis defined by the second segment 416. The stiffness k of the deformable portion 418 is selected/tuned such that it deforms allowing the second segment 416 to engage the detection switch 413 as the monopolar connector 408 is inserted and engaged with the contact 406. Thus, once fully inserted, the monopolar connector 408 deflects the first segment 414, which flexes the second segment 416, which in turn, actuates the detection switch 413, which is actuatable in the direction "A" (FIG. 5). Conversely, the monopolar connector 408 being partially inserted only partially deflects the first segment 414, which would not flex the second segment 416 sufficiently to engage the detection switch 413.

In addition, the deformable portion 418 allows the activation link 412 to be decoupled from the detection switch 413, allowing the force applied to the detection switch 413 to be limited to a level that will not break it even if different diameter monopolar connectors 408 are attached.

The detection switch 413 is electrically coupled to a control circuit 422 of the monopolar drive unit 400, such that upon activation, the control circuit 422 receives a signal from the detection switch 413 in response to engagement by the activation link 412. The monopolar drive unit 400 then communicates with the control device 4 and/or the generator 200, indicating that the monopolar electrosurgical instrument 10' is electrically coupled to the monopolar receptacle 404. The control device 4 and/or the generator 200 may then enable specific operational modes associated with the monopolar electrosurgical instrument 10'. In addition, the control device 4 and/or the generator 200 may also output an indication to the user that the monopolar electrosurgical instrument 10' is connected and is available for use.

Figure 6:
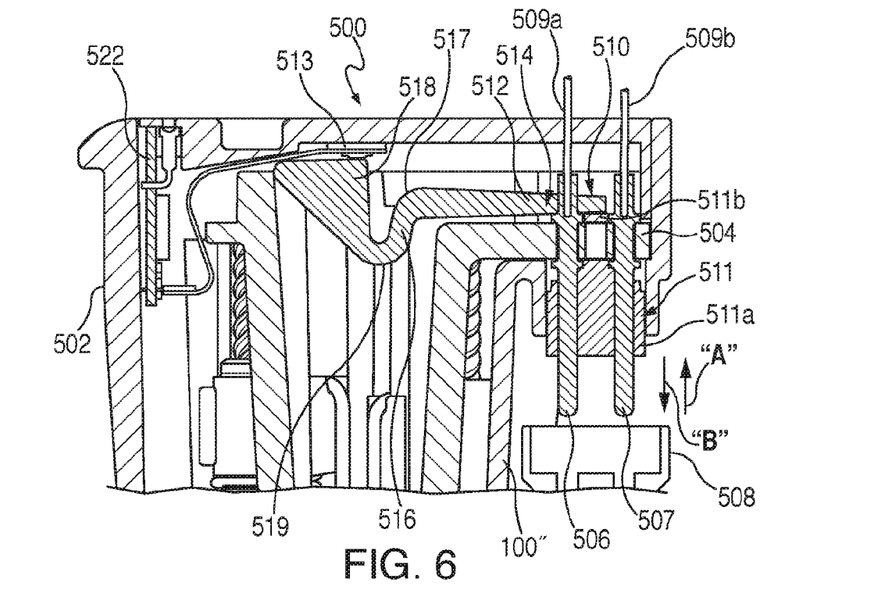
FIG. 6 is a side, cross-sectional view of a bipolar connector shown in a disconnected configuration.
Figure 7:
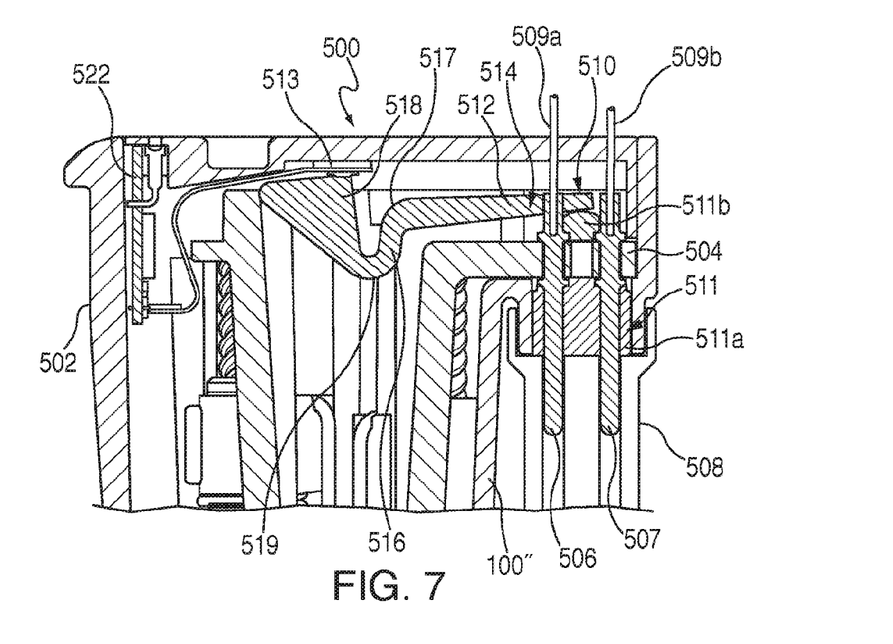
FIG. 7 is a side, cross-sectional view of the bipolar connector of FIG. 6 shown in a connected configuration.

With reference to FIGS. 6 and 7, a bipolar drive unit 500 is shown. The bipolar drive unit 500 includes a drive unit housing 502, which receives the actuation mechanism 100" of the electrosurgical instrument 10". The bipolar drive unit 500 also includes a bipolar receptacle 504 electrically coupled to the generator 200 through the cable 240 (FIG. 2). The bipolar receptacle 504 includes an active contact 506 and a return contact 507, which are configured to couple to a bipolar connector 508, thereby electrically connecting active electrode 34 and return electrode 36 (FIG. 2), respectively, of the bipolar electrosurgical instrument 10" to the generator 200. The active and return contacts 506 and 507 are coupled to leads 509a and 509b, respectively, thereby, electrically connecting active electrode 34 and return electrode 36 (FIG. 2) of the bipolar electrosurgical instrument 10" to the active and return contacts 506 and 507.

The bipolar drive unit 500 also includes a detection assembly 510, which is substantially similar to the detection assembly 410. The detection assembly 510 includes a connector link 511 and an activation link 512 configured to engage a detection switch 513 disposed on an inner wall of the drive unit housing 502. In embodiments, the detection switch 513 may be disposed on any surface within the drive unit housing 502 where it may be actuated by the activation link 512.

The connector link 511 includes a distal portion 511a configured to engage the bipolar connector 508 and a proximal portion 511b configured to engage the activation link 512. In particular, the connector link 511 is configured to move in the same direction as insertion direction "A" (FIG. 6) of the bipolar connector 508. In embodiments, the connector link 511 may include a spring (not shown) or act as a spring, which biases the connector link 511 in a direction "B," which is opposite the direction "A." In further embodiments, the connector link 511 may be coupled to the bipolar drive unit 500.

The activation link 512 includes a first segment 514 configured to engage the connector link 511. The activation link 512 also includes a middle segment 516 and a second segment 518 configured to engage the detection switch 513. The first segment 514 is interconnected to the middle segment 516 via a first curved portion 517 and the middle segment 516 is interconnected to the second segment 518 via a second curved portion 519. The activation link 512 may be formed from any suitable flexible or resilient non-conductive material such as polymers.

During use, the bipolar connector 508 is inserted in the direction "A" until fully engaging (e.g., inserted fully into) the bipolar receptacle 504, thereby electrically coupling with the active and return contacts 506 and 507. The bipolar connector 508 also engages the distal end 511a of the connector link 511, such that the proximal portion 511b of the connector link 511 engages the first segment 514 of the activation link 512. This engagement pushes the first segment 514 in the direction "A." This in turn, bends activation link 512 at the first curved portion 517 between the first segment 514 and the middle segment 516 and the second curved portion 519 between the middle segment 516 and the second segment 518. Since the first segment 514 is fully compressed, the mechanical strain is transferred to the second segment 518 through the first and second curved portions 517 and 519 and the middle segment 516.

Similarly to the activation link 412, the activation link 512 may also have a predetermined stiffness, k, as defined by a formula (I):

$$k=F/\delta \quad \quad (I)$$

In formula (I), F is the force applied to the activation link 512 and δ is a displacement (e.g., distance) in a direction perpendicular to a longitudinal axis defined by the first segment 514. The stiffness k of the activation link 512 is selected/tuned such that it deforms allowing for variation in engagement of the bipolar connector 508 and prevent mechanical overload of the detection switch 513. Thus, once fully inserted, the bipolar connector 508 deflects the first segment 514, which flexes the middle segment 516 and pushes the second segment 518 in the direction "A," which in turn, engages the detection switch 513 (FIG. 7). Conversely, the bipolar connector 508 being partially inserted only partially deflects the first segment 514, which would not flex the middle segment 516 sufficiently to engage the detection switch 513.

The detection switch 513 is electrically coupled to a control circuit 522 of the bipolar drive unit 500, such that upon activation, the control circuit 522 receives a signal from the detection switch 513 in response to engagement by the activation link 512. The bipolar drive unit 500 then communicates with the control device 4 and/or the generator 200, indicating that the bipolar electrosurgical instrument 10" is electrically coupled to the bipolar receptacle 504. The control device 4 and/or the generator 200 may then enable certain operational modes associated with the bipolar electrosurgical instrument 10". In addition, the control device 4 and/or the generator 200 may also output an indication to the user that the bipolar electrosurgical instrument 10" is connected and is available for use.

It will be understood that various modifications may be made to the embodiments disclosed herein. In embodiments, the detection assemblies 410 and 510 may be used interchangeably with monopolar and bipolar receptacles 404 and 504 or any other electrical connectors, by changing the number of contacts being used. Therefore, the above description should not be construed as limiting, but merely as exemplifications of various embodiments. Those skilled in the art will envision other modifications within the scope and spirit of the claims appended thereto.

What is claimed is:

1. A robotic surgical system comprising:
  an electrosurgical generator;
  an electrosurgical instrument including an electrosurgical connector; and
  a robotic arm including an instrument drive unit coupled to the electrosurgical instrument, the instrument drive unit including a drive unit housing having:
    an electrosurgical receptacle coupled to the electrosurgical generator and configured to engage the electrosurgical connector;
    an activation link including:
      a first segment engageable by the electrosurgical connector;
      a second segment; and
      a bent portion interconnecting the first segment and the second segment, wherein the first and second segments are configured to flex about the bent portion; and
    a detection switch actuatable by the actuation link second segment upon the first segment being engaged by the electrosurgical connector.

2. The robotic surgical system according to claim 1, wherein the electrosurgical instrument is a monopolar electrosurgical instrument and the electrosurgical receptacle includes an electrical contact configured to couple to the electrosurgical connector.

3. The robotic surgical system according to claim 1, wherein the electrosurgical instrument is a bipolar electrosurgical instrument and the electrosurgical receptacle includes an active contact and a return contact that are configured to electrically couple to the electrosurgical connector.

4. The robotic surgical system according to claim 1, wherein at least one of the first segment or the second segment includes a deformable portion that flexes in response to the first segment being engaged by the electrosurgical connector being fully inserted into the electrosurgical receptacle.

5. The robotic surgical system according to claim 1, wherein the first segment includes a protrusion disposed in a path of engagement by the electrosurgical connector and configured to contact the electrosurgical connector.

6. The robotic surgical system according to claim 1, wherein the drive unit housing further includes a biased connector link engageable by the electrosurgical connector.

7. The robotic surgical system according to claim 6, wherein the first segment of the activation link is engageable by the connector link.

* * * * *